United States Patent
Stewart et al.

[11] Patent Number: 5,931,824
[45] Date of Patent: Aug. 3, 1999

[54] IDENTIFICATION AND ACCOUNTABILITY SYSTEM FOR SURGICAL SPONGES

[76] Inventors: William W. Stewart, 426 N. Foy's Rd., Kalispell, Mont. 59901; Brian E. Stewart, 11982 Kiowa 306, Los Angeles, Calif. 90049

[21] Appl. No.: 08/921,430

[22] Filed: Aug. 29, 1997

Related U.S. Application Data

[60] Provisional application No. 60/025,629, Sep. 4, 1996.

[51] Int. Cl.[6] ............................ A61F 13/15; A61F 13/20
[52] U.S. Cl. ............................................. 604/358; 604/362
[58] Field of Search ..................................... 604/358, 362, 604/385.1

[56] References Cited

U.S. PATENT DOCUMENTS

| | | | |
|---|---|---|---|
| 3,941,132 | 3/1976 | Lenaghan | 604/377 |
| 3,965,907 | 6/1976 | Hardy et al. | |
| 4,098,728 | 7/1978 | Rosenblatt | |
| 4,114,601 | 9/1978 | Abels | |
| 4,244,369 | 1/1981 | McAvinn et al. | |
| 4,477,256 | 10/1984 | Hirsch | 604/362 |
| 4,626,251 | 12/1986 | Shen | 604/362 |
| 4,639,253 | 1/1987 | Dyer et al. | 604/362 |
| 4,645,499 | 2/1987 | Rupinskas | 604/362 |
| 4,658,818 | 4/1987 | Miller et al. | 604/362 |
| 4,718,897 | 1/1988 | Elves | 604/362 |
| 4,832,198 | 5/1989 | Alikhan | 206/438 |
| 4,917,694 | 4/1990 | Jessup | 604/362 |
| 5,031,642 | 7/1991 | Nosek | 128/906 |
| 5,041,103 | 8/1991 | Rupinskas | 604/362 |
| 5,045,080 | 9/1991 | Dyer et al. | 604/362 |
| 5,049,219 | 9/1991 | Johns et al. | 156/73.1 |
| 5,112,325 | 5/1992 | Zachry | 604/362 |

*Primary Examiner*—Mark O. Polutta

[57] ABSTRACT

An automatic identification system for accounting for and identifying a plurality of surgical sponges used during a surgical procedure. Machine-readable information is located on a plurality of surgical sponges. Each sponge of the plurality of surgical sponges has unique machine-readable information located thereon. The unique machine-readable information is unique for at least one surgical procedure.

28 Claims, 2 Drawing Sheets

IDENTIFICATION AND ACCOUNTABILITY SYSTEM FOR SURGICAL SPONGES

This application is a provision of Ser. No. 60/025,629 filed Sep. 4, 1994.

BACKGROUND OF THE INVENTION

1. Field of the Invention

The present invention relates to an identification and accountability system for surgical sponges and more particularly to an identification and accountability system for surgical sponges, which utilizes machine-readable information to identify and account for surgical sponges.

2. Description of the Related Art

Surgical sponges are commonly used during surgical procedures to absorb body fluids, mostly blood, of the patient both inside the incision and around the site of surgery. Sponges of this nature are usually made of an open ended absorbic fabric, such as woven cotton. When used, surgical sponges become saturated with blood, alter in size and shape and therefore become hard to distinguish from body tissue and each other. For this reason surgical sponges are hard to identify and account for both during and after a surgical procedure. This problem becomes magnified in larger surgical procedures where there are a large number of sponges used.

Before any particular surgical procedure all surgical items must be meticulously counted. After the procedure all items used in that particular surgery must be identified and accounted for. Surgical sponges are a difficult item to account for before, during and especially after a surgical procedure. The current method of identification and accountability relies on medical personnel to count these items by hand, relying on human visual detection and counting ability to differentiate one sponge from another and account for all the sponges, leaving this method open to a degree of human error. If a sponge count taken during or after a surgical procedure does not match a sponge count taken during or after the same procedure, the sponges are impregnated with an x-ray detectable element so that the patient can be x-rayed to see if the missing sponge or sponges are inside the patient and where.

The current system of accountability and identification for surgical sponges has proven itself unreliable and inefficient. Not only does the large amount of time involved to differentiate the sponges from one another and account for them all lead to large costs, but also the unreliable nature of the method leads to an alarming number of miscounted sponges resulting in retained surgical sponges inside the patient. These unfortunate incidents adversely affect not only the health of the patient, but also prove costly to the nurses, technicians, doctors, hospitals and insurance companies involved.

Past attempts have been made to increase the chances of accurate visual counting of surgical sponges. U.S. Pat. No. 4,917,694 addressed this problem by including, in the sponge, an elongated visually detectable element at a visible location on the sponge comprising a pair of elongated twisted strands. One of the strands contrasts with the color of the sponge, and the other with the color of blood. This is done to facilitate visual detection of the sponge whether it is dry or soaked with blood. This is done to facilitate visual detection of the sponge and counting ability and is therefore subject to a high degree of human error. There is no attempt to differentiate one individual sponge from another.

U.S. Pat. No. 4,114,601 attempts to solve the problem of medical item detection. It describes a method by which surgical implants, instruments, sponges, implantable devices and indwelling therapeutic devices and materials may be detected within the human body, or other area of interest, by incorporating or adding a radio frequency transponder. Non-linear mixing of two frequencies in a radio transponder is used. This transponder may be a small film deposition of ferrite material exhibiting gyro-magnetic resonance at selected frequencies or a solid state device. When the transponders are incorporated in the items, the detection of the transponder is equivalent to the detection of the implant.

U.S. Pat. No. 5,031,642 also attempts to address the issue of medical item accountability. The invention is an "Integrator Collector" containing a time-correlated digital receiver for measuring, displaying and recording fluid loss from surgery and for maintaining, displaying and recording a count of secured items, such as needles and sponges by means of an electronic beam, which upon activation by a surgical sponge, triggers the automatic conversion of the weight of the items into cubic centimeters of blood loss.

The '642 patent calls for the placement of indicia on external packaging of the containers holding the surgical sponges as a means to count the number of sponges before a surgical procedure, but makes no attempt to include this indicia on the individual sponges themselves. No attempt is made to differentiate one individual sponge from the next by means of indicia.

OBJECTS AND SUMMARY OF THE INVENTION

It is therefore a principal object of the present invention to account for and identify surgical sponges in an efficient, reliable manner.

It is another object to provide an identification and accountability system for surgical sponges which is not obscured by the conditions that the system will be exposed to in its use, particularly exposure to body fluids including but not limited to blood.

It is another object to provide an identification and accountability system for surgical sponges which does not compromise any medical requirements thereof, particularly but not limited to requirements of sterility.

It is another object to provide this identification and accountability system in a way as not to compromise the function of the surgical sponges.

These and other objects are achieved by the present invention that, in one broad aspect, comprises machine-readable information located on individual surgical sponges. The machine-readable information is unique to each individual surgical sponge, making each and every sponge automatically differentiable from the next for at least a given surgical procedure. Each surgical sponge further preferably includes an x-ray detectable element.

Means are provided for automatically reading the individually unique surgical sponges and creating an inventory of the surgical sponges to be used for a particular procedure. An automated check of the inventory of surgical sponges can be obtained at any desired time before, during or after a surgical procedure.

The present invention provides for the improved identification and accountability of surgical sponges by the incorporation of automatic identification technology to these sponges in a manner that allows for the differentiation of the individual sponges from each other. This is done through the impregnation of unique machine-readable information to each individual sponge that is unique for at least a surgical procedure. By the incorporation of automatic identification and recognition technology described herein, the human error factor which so negatively affects the current method of identification and accountability and differentiation will be greatly reduced.

By replacing the need to rely solely on human visual detection and counting ability to differentiate the individual sponges from one another and account for their presence or lack thereof with a system as presented here, the medical community will be empowered with the ability to identify and account for individual surgical sponges in a vastly superior way.

In accordance with the present invention, each surgical sponge is made individually unique for a given surgical procedure and preferably from every other surgical sponge by assigning unique machine-readable information to each individual surgical sponge. The sponges therefore become distinguishable from each other in an automated manner providing for a more accurate and efficient system of identification and accountability of these medical items. The inventory of unique surgical sponges created by the automated system before a surgical procedure via a scanning device which reads the machine-readable information off the sponges and inputs that information into a computer system can be compared to an inventory created either during or after the same procedure and an instant comparison of inventories be made to determine the presence, or lack thereof, of all the individual sponges.

Through the use of the herein described system, medical personnel will be able to not only determine if a sponge or sponges are missing faster and more reliably, but exactly which sponge or sponges are missing. This process may lessen the need for needlessly exposing a patient to x-ray radiation and further trauma by needless closing and reopening of an incision. This system will have the potential to vastly reduce the occurrence of retained surgical sponges. Furthermore, the automatically created inventories of surgical sponges can be logged, becoming a permanent addition to a patient's medical file, and referenced at a later time for such needs as legal or medical reference. This herein described system will empower the medical community with the ability to raise the overall standard of health care while potentially saving costs for all parties involved from the patient, medical personnel, hospitals and insurance companies.

Other objects, advantages, and novel features will become apparent from the following detailed description of the invention when considered in conjunction with the accompanying drawings.

BRIEF DESCRIPTION OF THE DRAWINGS

The same reference characters designate the same parts or elements throughout the drawings.

DETAILED DESCRIPTION OF THE PREFERRED EMBODIMENTS

Figure 1:
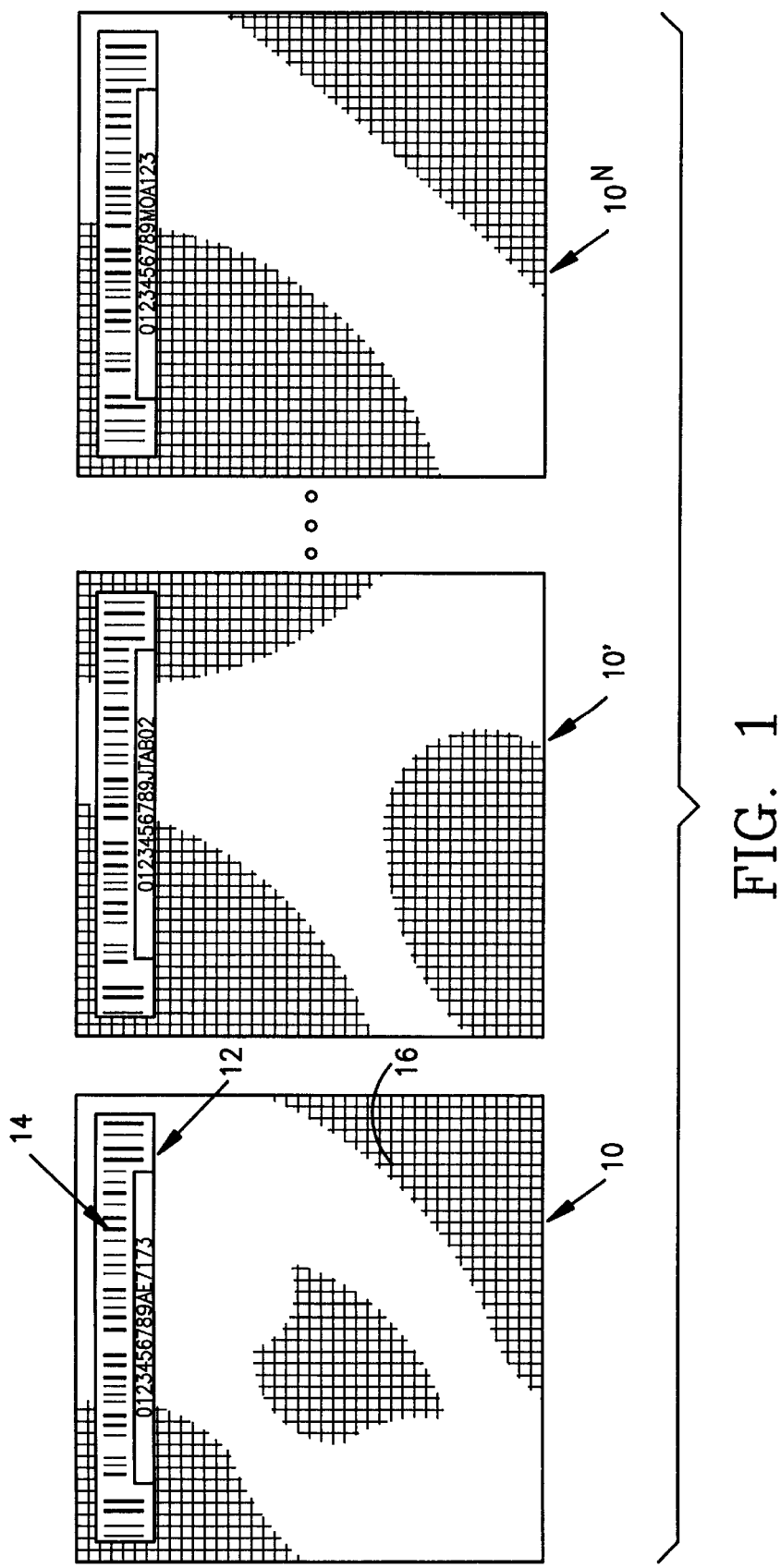
FIG. 1 illustrates a preferred embodiment of the surgical sponge system of the present invention.

Referring now to the drawings and the characters of reference marked thereon, FIG. 1 illustrates the preferred embodiment of the surgical sponge system of the present invention, the sponges being designated generally by numeral designations $10, 10', \ldots 10^N$. Each sponge 10 includes a substrate 12 having unique machine-readable information 14 located thereon. This sponge material 16 may be conventional surgical sponge material, typically, folded woven cotton.

The substrate 12 is formed of inert, sterilizable material, which is capable of maintaining the machine-readable information 14. It may be, for example, cotton, polyester or a blend thereof. These materials do not inhibit the basic function of the sponge 16. Various label designers and manufacturers which may fabricate suitable labels for use as substrates 12 may include Computype Inc., St. Paul, Minn.; Information Plus Corp., Texas; and Polymark, Inc., Cincinnati, Ohio.

Figure 2:
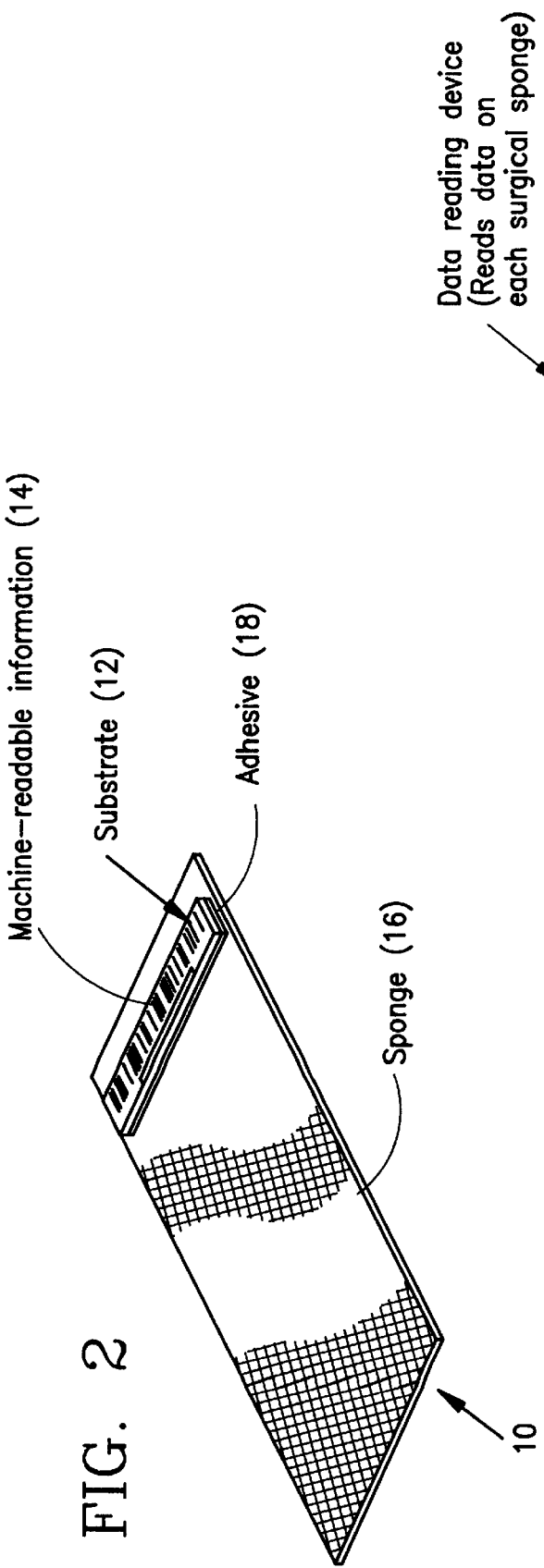
FIG. 2 is a side perspective view of a sponge incorporating the features of the present invention.

Referring now to FIG. 2, it can be seen that the lower surface of the substrate 12 includes a layer of adhesive material 18 for attaching the substrate 12 to the sponge material 16. The adhesive material 18 is preferably of the type that provides attachment by application of heat thereto. The above-mentioned label manufacturers typically use such adhesive materials. However, the present invention preferably involves the addition of an x-ray detectable element in the adhesive material 18. Such an x-ray detectable element may include barium sulfate.

It is understood that although the x-ray detectable element has been described as being contained within the adhesive material 18, it may alternately be included on the sponge material 16.

The machine-readable information 14 on each sponge is unique for at least one surgical procedure. The machine-readable information 14 is preferably presented in bar code form. It may be presented by commercially available inkjet technology or thermal transfer processes. Examples of companies providing these capabilities include, for example, Computype, Inc.; Zebra, Inc., Vernon Hills, Ill.; and Information Plus Corporation.

Although the machine-readable information 14 is unique for at least one surgical procedure, it is preferably absolutely unique; i.e. no two sponges will contain the same information, even in different surgical procedures.

The machine-readable information 14 may be present in either one, two or three-dimensional technologies in one of various commercially viable forms.

A sponge may include unique human-readable information thereon associated with its respective unique machine-readable information. This human-readable information is provided as a backup method if there is a machine failure in reading the information in its machine-readable form.

Figure 3:
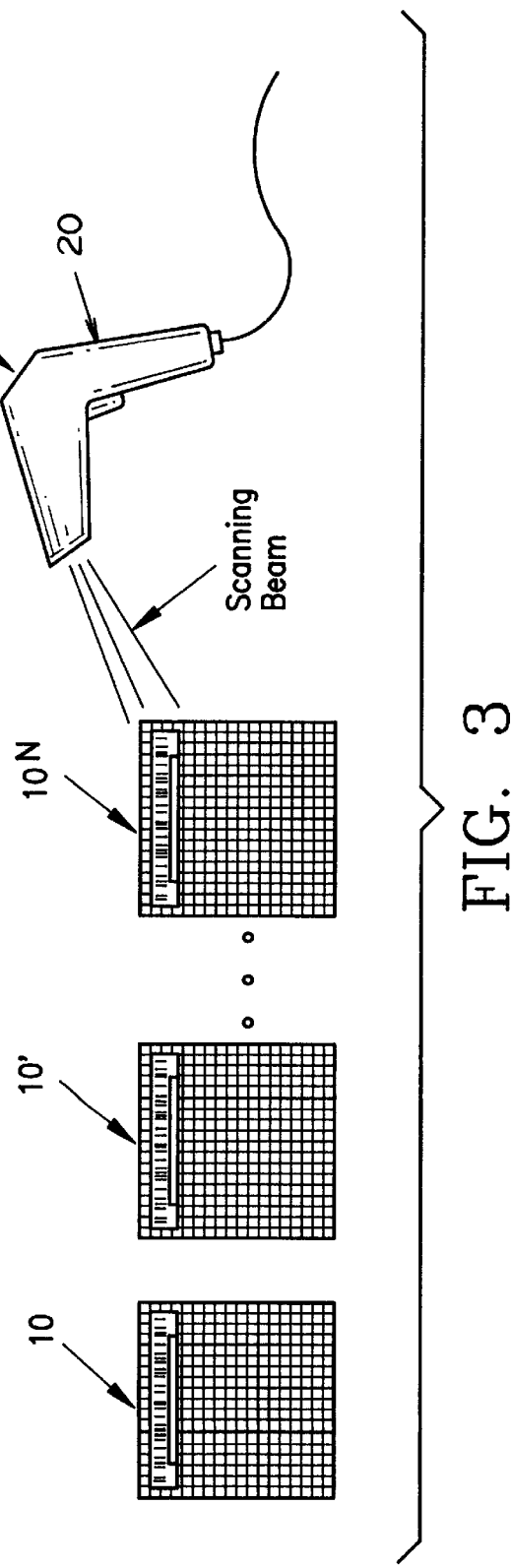
FIG. 3 illustrates the use of a scanner for reading the data on the surgical sponges.

Referring now to FIG. 3, sponges $10, 10', \ldots 10^N$, are shown being scanned by a data reading device 20. The data reading device 20 is connected to a computer (not shown). The data reading device 20 may be, for example, a bar code scanner. Before each surgical procedure, an inventory is created of the surgical sponges to be used for that particular procedure. To account for and identify the surgical sponges either during or after this surgical procedure another inventory can be created by scanning the sponges to check and see if they are all accounted for. The missing sponge(s) can be identified.

Obviously, many modifications and variations of the present invention are possible in light of the above teachings. It is, therefore, to be understood that within the scope of the appended claims, the invention may be practiced otherwise than as specifically described.

What is claimed and desired to be secured by Letters Patent of the United States is:

1. An automatic identification system for use with a reading device, said automatic identification system for accounting for and identifying a plurality of surgical sponges used during a surgical procedure, comprising:

machine-readable information located on a plurality of physically unconnected surgical sponges, wherein each sponge of said plurality of surgical sponges has its own differentiating machine-readable information located thereon which will not repeat on any other sponge used in a given surgical procedure, said machine-readable information being readable by a reading device, wherein the physically unconnected surgical sponges can be recognized and accounted for during a surgical procedure without reliance on human visual detection and counting ability to identify. differentiate and account for the surgical sponges.

2. The automatic identification system of claim 1, wherein said unique machine-readable information is located on a substrate, said substrate positioned on a respective surgical sponge.

3. The automatic identification system of claim 1, wherein each said surgical sponge further includes an x-ray detectable element.

4. The automatic identification system of claim 1, wherein said machine-readable information is contained within said surgical sponge.

5. The automatic identification system of claim 1, wherein said machine-readable information is contained on said surgical sponge.

6. The automatic identification system of claim 1, wherein each of said plurality of surgical sponges further comprises unique human-readable information thereon associated with its respective unique machine-readable information.

7. The automatic identification system of claim 1, wherein said information is made to be body fluid repellant to prevent obscuration thereof during reading.

8. The automatic identification system of claim 7, wherein said substrate comprises a thin film.

9. The automatic identification system of claim 2, wherein said substrate is formed of inert material.

10. The automatic identification system of claim 1, wherein said machine-readable information comprises bar code information.

11. The automatic identification system of claim 1, wherein said machine-readable information comprises compressed symbology.

12. The automatic identification system of claim 1, wherein said unique machine readable information is located on a substrate, said substrate positioned on a respective sponge, said substrate comprising an adhesive for attaching said substrate to the surgical sponge.

13. The automatic identification system of claim 12, wherein said adhesive comprises an x-ray detectable element.

14. The automatic identification system of claim 13, wherein said x-ray detectable element comprises barium sulfate.

15. The automatic identification system of claim 12, wherein said adhesive is of a type which provides attachment by the application of heat thereto.

16. The automatic identification system of claim 1, wherein said machine readable information is located on a substrate, said substrate being positioned on a respective sponge, said substrate comprising biologically inert material.

17. A surgical sponge system for accounting for and identifying a plurality of surgical sponges used during a surgical procedure, comprising:

a plurality of surgical sponges, each sponge having unique machine readable information located thereon, wherein said unique machine readable information is unique for at least one surgical procedure.

18. The automatic identification system of claim 17, wherein said unique machine-readable information is located on a substrate, said substrate positioned on a respective surgical sponge.

19. The automatic identification system of claim 17, wherein each said surgical sponge further includes an x-ray detectable element.

20. The automatic identification system of claim 17, wherein said machine-readable information is contained within said surgical sponge.

21. The automatic identification system of claim 17, wherein said machine-readable information is contained on said surgical sponge.

22. The automatic identification system of claim 17, wherein each of said plurality of surgical sponges further comprises unique human-readable information thereon associated with its respective unique machine-readable information.

23. The automatic identification system of claim 17, wherein said information is made to be body fluid repellant to prevent obscuration thereof during reading.

24. The automatic identification system of claim 23, wherein said substrate comprises a thin film.

25. The automatic identification system of claim 18, wherein said substrate is formed of inert material.

26. The automatic identification system of claim 17, wherein said machine-readable information comprises bar code information.

27. The automatic identification system of claim 17, wherein said machine-readable information comprises compressed symbology.

28. The automatic identification system of claim 17, wherein said unique machine readable information is located on a substrate, said substrate positioned on a respective sponge, said substrate comprising an adhesive for attaching said substrate to the surgical sponge.

* * * * *

UNITED STATES PATENT AND TRADEMARK OFFICE
CERTIFICATE OF CORRECTION

PATENT NO. : 5,931,824
DATED : 08/03/99
INVENTOR(S) : WILLIAM W. STEWART and BRIAN E. STEWART It is certified that error appears in the above-identified patent and that said Letters Patent is hereby corrected as shown below:

Column 5, Line 17, after "identify" delete "." and substitute therefor -- , --.

Signed and Sealed this

Twenty-fifth Day of April, 2000

Attest:

Q. TODD DICKINSON

*Attesting Officer*  *Director of Patents and Trademarks*

(12) EX PARTE REEXAMINATION CERTIFICATE (6311th)
United States Patent
Stewart et al.

(10) Number: US 5,931,824 C1
(45) Certificate Issued: Jul. 22, 2008

(54) IDENTIFICATION AND ACCOUNTABILITY SYSTEM FOR SURGICAL SPONGES

(76) Inventors: William W. Stewart, 426 N. Foy's Rd., Kalispell, MT (US) 59901; Brian E. Stewart, 11982 Kiowa 306, Los Angeles, CA (US) 90049

Reexamination Request:
No. 90/007,051, May 21, 2004

Reexamination Certificate for:
Patent No.: 5,931,824
Issued: Aug. 3, 1999
Appl. No.: 08/921,430
Filed: Aug. 29, 1997

Certificate of Correction issued Apr. 25, 2000.

Related U.S. Application Data

(60) Provisional application No. 60/025,629, filed on Sep. 4, 1996.

(51) Int. Cl.
*A61F 13/15* (2006.01)
*A61F 13/20* (2006.01)

(52) U.S. Cl. ........................................ 604/368; 604/362
(58) Field of Classification Search .................... 604/362
See application file for complete search history.

(56) References Cited

U.S. PATENT DOCUMENTS

| | | | | | |
|---|---|---|---|---|---|
| 3,481,462 | A | * | 12/1969 | Chapel | 206/438 |
| 3,915,172 | A | * | 10/1975 | Wichterle et al. | 604/8 |
| 3,948,390 | A | * | 4/1976 | Ferreri | 206/370 |
| 4,105,115 | A | * | 8/1978 | Horvath et al. | 206/370 |
| 4,105,800 | A | * | 8/1978 | Jahns et al. | 426/61 |
| 4,264,575 | A | * | 4/1981 | Zimmerman et al. | 424/432 |
| 4,355,020 | A | * | 10/1982 | Kuy | 424/404 |
| 4,477,256 | A | * | 10/1984 | Hirsch | 604/362 |
| 4,711,996 | A | * | 12/1987 | Drexler | 235/468 |
| 4,889,230 | A | * | 12/1989 | Zachry | 206/362 |
| 4,943,939 | A | * | 7/1990 | Hoover | 702/128 |
| 5,057,095 | A | | 10/1991 | Fabian | |
| 5,074,840 | A | * | 12/1991 | Yoon | 604/15 |
| 5,231,273 | A | * | 7/1993 | Caswell et al. | 235/385 |
| 5,374,813 | A | * | 12/1994 | Shipp | 235/375 |
| 5,443,082 | A | | 8/1995 | Mewburn | |
| 5,456,718 | A | | 10/1995 | Szymaitis | |
| 5,554,841 | A | * | 9/1996 | Kost et al. | 235/494 |
| 5,610,811 | A | * | 3/1997 | Honda | 705/2 |
| 5,629,498 | A | * | 5/1997 | Pollock et al. | 177/15 |
| 5,637,850 | A | * | 6/1997 | Honda | 235/454 |
| 5,650,596 | A | * | 7/1997 | Morris et al. | 177/25.13 |
| 5,678,569 | A | * | 10/1997 | Chew et al. | 128/897 |
| 5,805,451 | A | * | 9/1998 | Speas et al. | 700/110 |
| 5,923,001 | A | * | 7/1999 | Morris et al. | 177/245 |
| 5,991,728 | A | * | 11/1999 | DeBusk et al. | 705/2 |
| 5,996,889 | A | * | 12/1999 | Fuchs et al. | 235/375 |
| 2002/0049650 | A1 | * | 4/2002 | Reff | 705/29 |

FOREIGN PATENT DOCUMENTS

| | | | |
|---|---|---|---|
| EP | 948940 A1 | * | 10/1999 |
| FR | 2580172 A1 | * | 10/1986 |
| GB | 884143 A | | 12/1961 |
| GB | 1274061 | * | 5/1975 |
| WO | WO 9115159 A1 | * | 10/1991 |
| WO | WO 9417767 A1 | * | 8/1994 |
| WO | WO 9422580 A1 | * | 10/1994 |
| WO | WO 9527252 A1 | * | 10/1995 |
| WO | WO 9830166 A1 | * | 7/1998 |

OTHER PUBLICATIONS

Translation of 94/17767.*

* cited by examiner

*Primary Examiner*—David O. Reip

(57) ABSTRACT

An automatic identification system for accounting for and identifying a plurality of surgical sponges used during a surgical procedure. Machine-readable information is located on a plurality of surgical sponges. Each sponge of the plurality of surgical sponges has unique machine-readable information located thereon. The unique machine-readable information is unique for at least one surgical procedure.

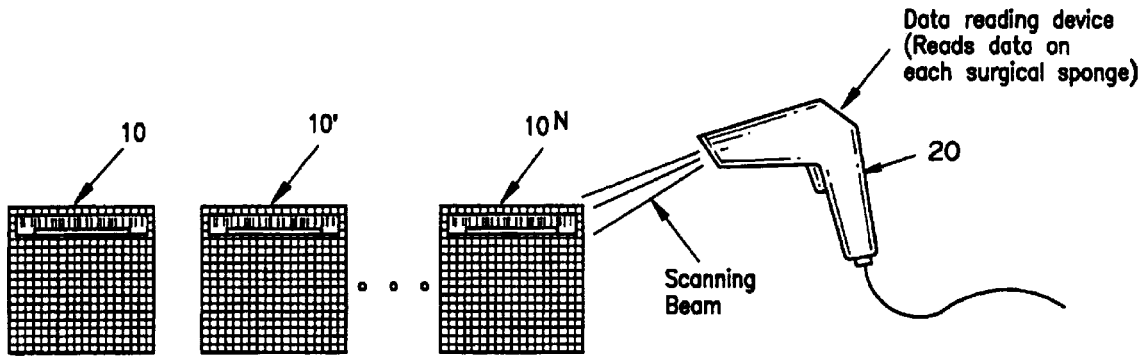

US 5,931,824 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 4–5:

This application is a [provision] *provisional* of Ser. No. 60/025,629 filed Sep. 4, [1994] *1996*.

AS A RESULT OF REEXAMINATION, IT HAS BEEN DETERMINED THAT:

Claims 4 and 20 are cancelled.

Claims 1, 8, 17 and 24 are determined to be patentable as amended.

Claims 2, 3, 5–7, 9–16, 18, 19, 21–23 and 25–28, dependent on an amended claim, are determined to be patentable.

New claims 29–40 are added and determined to be patentable.

1. An automatic identification system for use with a reading device, said automatic identification system for accounting for and identifying a plurality of surgical sponges used during a surgical procedure, comprising:
    machine-readable information located on a plurality of physically unconnected surgical sponges, wherein each sponge of said plurality of surgical sponges has its own differentiating machine-readable information located thereon *and which is different from and* which will not repeat on any other sponge used in a given surgical procedure, said machine-readable information being readable by a reading device, wherein the physically unconnected surgical sponges can be recognized and accounted for during a surgical procedure without reliance on human visual detection and counting ability to identify, differentiate and account for the surgical sponges.

8. The automatic identification system of claim [7] *2*, wherein said substrate comprises a thin film.

17. A surgical sponge system for accounting for and identifying a plurality of surgical sponges used during a surgical procedure, comprising:
    a plurality of surgical sponges, each sponge having a unique [machine readable] *machine-readable* information located thereon *and which is not repeated on any other of the plurality of sponges*, wherein said unique [machine readable] *machine-readable* information is unique for at least one surgical procedure.

24. The automatic identification system of claim [23] *18*, wherein said substrate comprises a thin film.

*29. An automatic identification system, said automatic identification system for accounting for and identifying a plurality of surgical sponges used during a surgical procedure, comprising:*
    *an automatic identification system according to claim 1; and*
    *a data reading device capable of reading the machine-readable information located thereon each surgical sponge.*

*30. The automatic identification system of claim 29, wherein the data reading device comprises a scanner having a scanning beam.*

*31. A surgical sponge system, comprising:*
    *a plurality of surgical sponges in a number sufficient to perform a given surgical procedure;*
    *wherein each surgical sponge in said plurality has unique machine-readable information located thereon and which distinguishes each individual surgical sponge from all other individual sponges in said plurality of sponges, wherein such machine-readable information is adapted to allow surgical sponges used in said given surgical procedure to be automatically scanned before the procedure and again during or after the procedure to identify missing surgical sponges.*

*32. The surgical sponge system of claim 31, wherein said unique machine-readable information is located on a substrate, said substrate positioned on the surface of a respective surgical sponge.*

*33. The surgical sponge system of claim 31, wherein each said surgical sponge further includes an x-ray detectable element.*

*34. The surgical sponge system of claim 31, wherein each of said plurality of surgical sponges further comprises unique human-readable information thereon associated with its respective unique machine-readable information.*

*35. The surgical sponge system of claim 31, wherein said information is made to be body fluid repellant to prevent obscuration thereof during reading.*

*36. The surgical sponge system of claim 32, wherein said substrate comprises a thin film.*

*37. The surgical sponge system of claim 32, wherein said substrate is formed of inert material.*

*38. The surgical sponge system of claim 31, wherein said machine-readable information comprises bar code information.*

*39. The surgical sponge system of claim 31, wherein said machine-readable information comprises compressed symbology.*

*40. The surgical sponge system of claim 31, wherein said unique machine-readable information is located on a substrate, said substrate positioned on a respective sponge, said substrate comprising an adhesive for attaching said substrate to the surgical sponge.*

\* \* \* \* \*